United States Patent
Codner et al.

(10) Patent No.: US 7,148,968 B2
(45) Date of Patent: Dec. 12, 2006

(54) PORTABLE SURFACE PLASMON RESONANCE IMAGING INSTRUMENT

(75) Inventors: Eric P. Codner, Madison, WI (US); Robert M. Corn, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 240 days.

(21) Appl. No.: 10/411,583

(22) Filed: Apr. 10, 2003

(65) Prior Publication Data

US 2004/0201848 A1  Oct. 14, 2004

(51) Int. Cl.
*G01N 21/55* (2006.01)
(52) U.S. Cl. .................................................... 356/445
(58) Field of Classification Search ................. 356/445
See application file for complete search history.

(56) References Cited

U.S. PATENT DOCUMENTS

| | | | | |
|---|---|---|---|---|
| 4,997,278 A | * | 3/1991 | Finlan et al. ............... | 356/128 |
| 5,313,264 A | * | 5/1994 | Ivarsson et al. ............. | 356/73 |
| 6,570,657 B1 | * | 5/2003 | Hoppe et al. ............... | 356/445 |
| 6,714,303 B1 | * | 3/2004 | Ivarsson .................... | 356/445 |
| 6,862,094 B1 | * | 3/2005 | Johansen ................... | 356/445 |
| 2003/0012693 A1 | * | 1/2003 | Otillar et al. .............. | 422/58 |

FOREIGN PATENT DOCUMENTS

WO            WO 01/69209        *  9/2001

* cited by examiner

*Primary Examiner*—Richard A. Rosenberger
(74) *Attorney, Agent, or Firm*—Boyle Fredrickson Newholm Stein & Gratz S.C.

(57) ABSTRACT

A surface plasmon resonant device provides practical portable operation through the use of a low power high efficiency LED source and a high-efficiency prism sample cell pre-loaded with probe molecules and sealed for field use. A simple mechanical control allows adjustment of angulation of the light and camera for accurate response outside of the laboratory.

20 Claims, 4 Drawing Sheets

PORTABLE SURFACE PLASMON RESONANCE IMAGING INSTRUMENT

STATEMENT REGARDING FEDERALLY SPONSORED RESEARCH OR DEVELOPMENT

This invention was made with United States Government support awarded by the following agency: DOD ARPA F30602-01-2-0555. The United States has certain rights in this invention.

CROSS-REFERENCE TO RELATED APPLICATIONS

BACKGROUND OF THE INVENTION

The present invention relates to instruments for chemical and biological analyses employing surface plasmon resonance, and in particular, to a portable version of such an instrument suitable for field use.

In surface plasmon resonance imaging, a sensor consisting of a thin metallic film is illuminated by polarized light of an appropriate wavelength and angle of incidence on a "reflecting" side of the film. The energy from the light couples to electrons of the metal of the film creating a resonant condition (surface plasmon resonance) that is highly sensitive to surface conditions on a "sensing" side of the film opposite the side that is illuminated.

Probe molecules are attached to the sensing side of the metallic film to selectively bind with target molecules in a solution to be analyzed. This binding, through the agency of the electron resonance in the film, causes a drop in reflectance of the reflecting side of the film. Detection of the decrease in reflected light thus provides a sensitive measurement of the binding of target molecules to the probe molecules, in turn providing an indication of the content of the solution being analyzed.

By placing a variety of different probe molecules on the sensing surface of the film, many different target molecules may be rapidly assessed. Importantly, the target molecules need not be labeled with fluorescent dye or the like prior to analysis.

Current surface plasmon resonance (SPR) equipment is large, complex, and expensive, and normally confined to use in a laboratory environment. A hand-held SPR device that could be easily transported to the field for remote measurements would be extremely valuable in assessing disease and detecting bio-terrorism and a variety of other analytic uses.

BRIEF SUMMARY OF THE INVENTION

The present inventors have developed a number of innovations that allow a standard SPR machine to be significantly reduced in size, cost, and electrical power consumption so that it may be rendered suitable for field use. Importantly, the inventors have determined that a standard narrow band LED may replace high-powered illumination sources previously used. An integral prism sample cell provides efficient light coupling to the metal film aiding in the use of the more energy efficient, but lower powered source. Construction of an integrated, disposable prism, metal film, and sample flow cell prevent contamination that may be incident to field use. Use of the low power light source together with a digitizing electronic camera allows the entire system to be operated using power and processing of a standard computer, for example, a laptop computer, readily available in or transportable to field locations.

Specifically then, the present invention provides a portable surface plasmon resonance imaging system having a sampling cell with a metallic film. The metallic film has probe molecules attached to a first side exposed to material flow through the sampling cell and a transparent support attached to a second side opposite the first side. An electronic camera positioned after a monochromatic filter receives reflected light from the second side of the metallic film originating at a light source constructed of a light emitting diode coupled with a polarizing element.

It is thus one object of the invention to provide an SPR device that may use a relatively low power, light-emitting diode (LED). The present inventors have determined that although the total luminance from an LED is far below that provided by white light sources in conventional SPR equipment, the narrow band concentration of the light energy from an LED, especially when used with additional features of the invention that provide improved light coupling, can be sufficient for SPR measurements.

The light emitting diode may be an infrared diode.

Thus, it is another object of the invention to maximize useable light energy by employing a high output LED emitting light frequencies to which standard electronic cameras are sensitive.

The invention may further include a cable connecting the electronic camera and the light source to a general purpose computer. The cable may include power leads communicating power from a power source contained in the computer to the electronic camera and the light source for powering the same. In at least one embodiment, the portable computer may be a laptop computer and the cable may be a universal serial bus (USB) cable.

Thus, it is another object of the invention to provide an interface drawing power from, and communicating data to, a standard computer, simplifying the design, improving portability and lowering cost. Use of a computer power supply, especially a laptop battery, is enabled by the low power light source of the LED.

The sampling cell may be a plastic prism having the metallic film attached to a first face of the prism.

Thus it is another object of the invention to provide a lightweight, disposable sampling system that provides extremely good light coupling so as to make best use of the light from the LED.

The prism may be held by a clamp removably holding the disposable prism in the optical path and the clamp may provide a fixed registration surface interfitting with at least two of the faces of the prism to fix the prism at a predefined location within the optical path.

Thus it is another object of the invention to provide a simple means for exchanging sample cells in the field making use of a clamp type structure with preset or fixed registration surfaces.

The prism may include an integral flow cell portion defining a cavity next to the side of the metallic film having the attached probe molecules for flow of sample material from a flow cell inlet to a flow cell outlet.

Thus it is another object of the invention to provide a wholly sealed sample chamber that may be disposed of after use and that does not require a clean environment for assembly, such as all would be difficult to obtain in the field.

The light source may be supported within the housing on a first swing arm pivoting in a radius about a point on the surface of the metallic film of the sampling cell to illuminate a region about the point through the transparent support of the sampling cell. Likewise, the electronic camera may be supported within the housing on a second swing arm pivoting in a radius about the point on the surface of the metallic film of the sampling cell and receiving reflective light from the second side of the metallic film. A mechanism between the first and second swing arms my move them simultaneously in symmetrical opposition about normal to the surface of the metallic film.

Thus it is another object of the invention to provide for simple and rapid adjustment of the angle of incidence and reflectance of the light beam to maximize sensitivity of the measurement.

An operator may have a first end communicating with the mechanism, and a second end accessible outside of the housing may be operated by one hand.

Thus it is another object of the invention to provide a system useable by a single individual in the field holding the device in one hand and operating the operator with their free hand.

These particular objects and advantages may apply to only some embodiments falling within the claims and thus do not define the scope of the invention.

DETAILED DESCRIPTION OF THE PREFERRED EMBODIMENT

Figure 1:
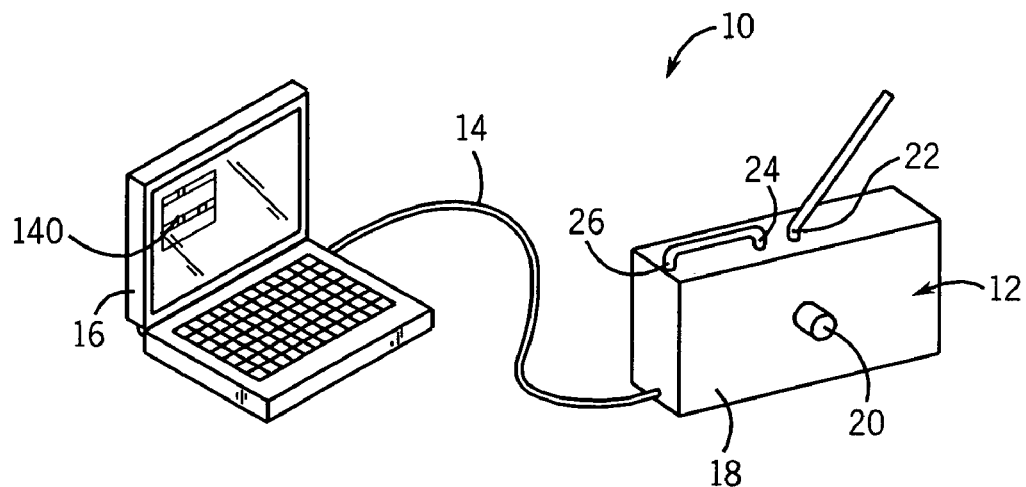
FIG. 1 is a perspective view of the portable SPR device of the present invention attached to a laptop computer for fieldwork.

Referring now to FIG. 1, a portable SPR device 10 includes an analyzer unit 12 attached, via a data and power cable 14, to a conventional laptop computer 16 or other standard computer system. The data and power cable 14 may, for example, be a universal serial bus (USB) cable such as provides a path allowing the analyzer unit 12 to receive power from the batteries or other power supply of the conventional laptop computer 16 and communicate data to the conventional laptop computer 16.

The analyzer unit 12 includes a generally box-shaped housing 18 such as may be comfortably held by an individual in one hand. An angulation knob 20, to be described in more detail below, extends from one vertical sidewall of the housing 18. A top wall of the housing 18 provides a sample inlet port 22 into which a sample for testing may be introduced and a sample outlet port 24 which may be connected to a self-contained vacuum port 26. The housing 18 is preferably of a rugged, opaque material, for example, aluminum or plastic.

Figure 2:
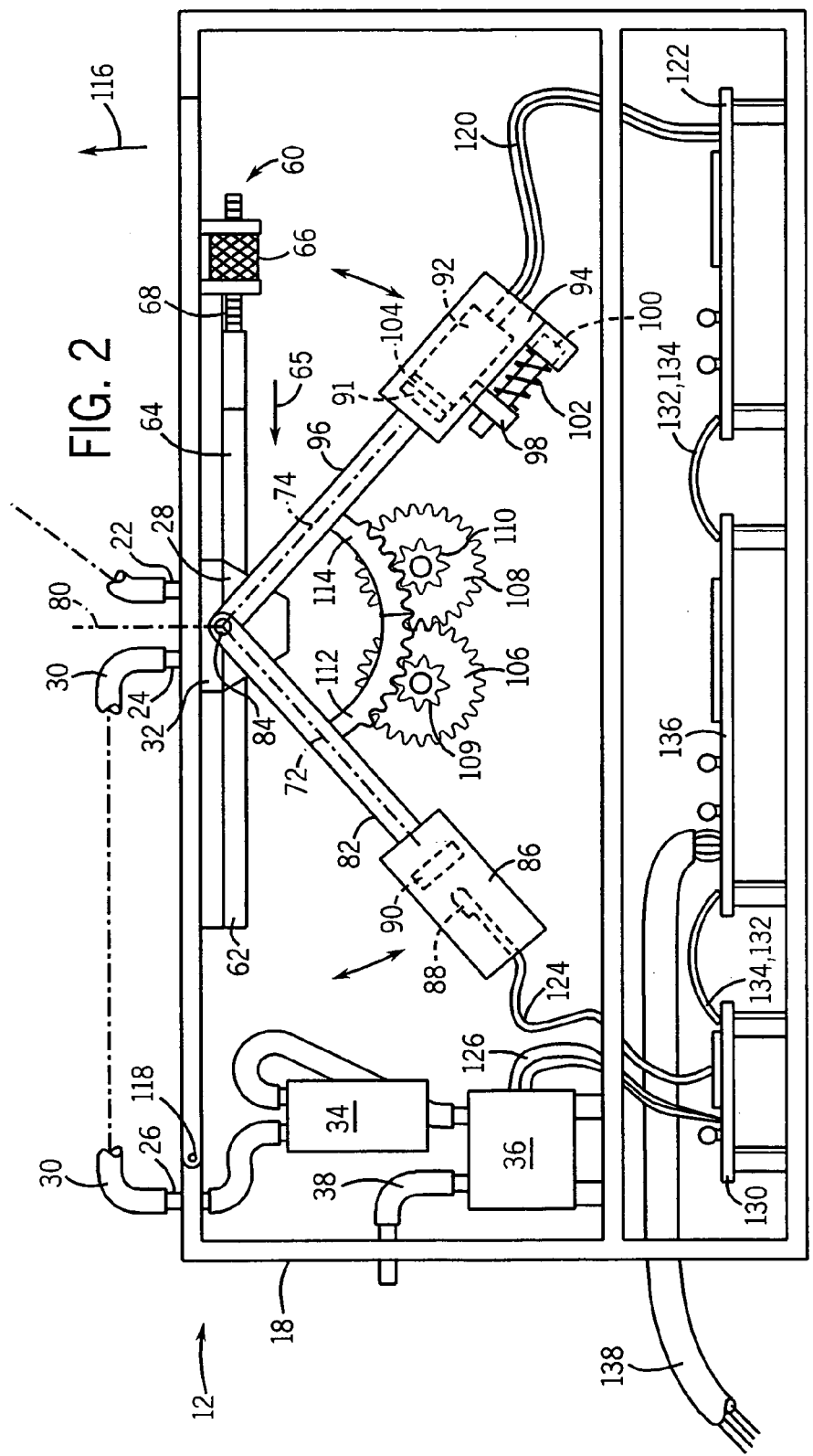
FIG. 2 is a front elevational view of the device of FIG. 1 with one side wall removed to show an internal sample cell, an angulation mechanism holding a solid state camera and LED light source, and a pump.

Referring now to FIG. 2, a sample including generally a carrier liquid such as water and molecules to be analyzed, may enter the sample inlet port 22, introduced by pipette or other instrument. The sample then passes through interface plate 32, exposed at the upper wall of the housing 18, to be received by an integrated test cell 28. From the integrated test cell 28, the sample passes to the sample outlet port 24 to be drawn through tubing 30 to the vacuum port 26. The vacuum port 26 communicates with a filter trap 34 trapping the sample and filtering liquid from air, the latter which passes through electric pump 36 to be exhausted via channel 38 through a side wall of the housing 18.

Figure 3:
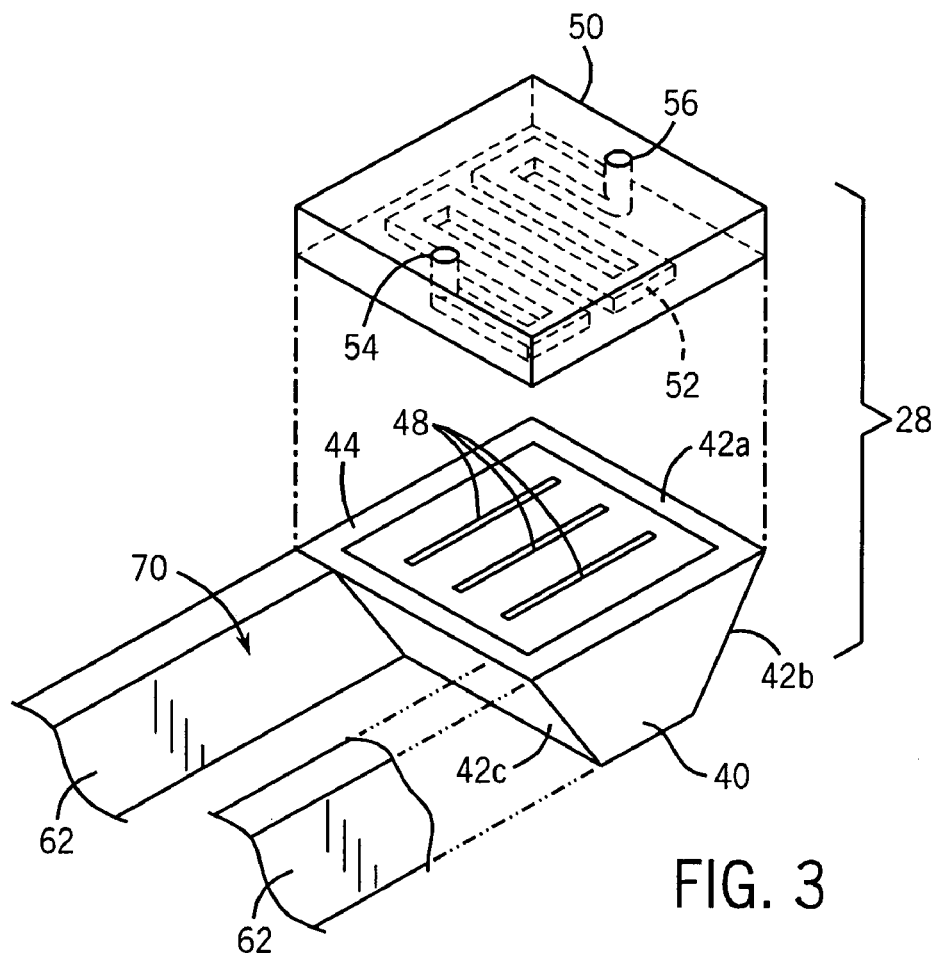
FIG. 3 is an exploded perspective view of the sample cell of FIG. 2, such as provides an integrated flow cell, metal film, and prism.
Figure 4:
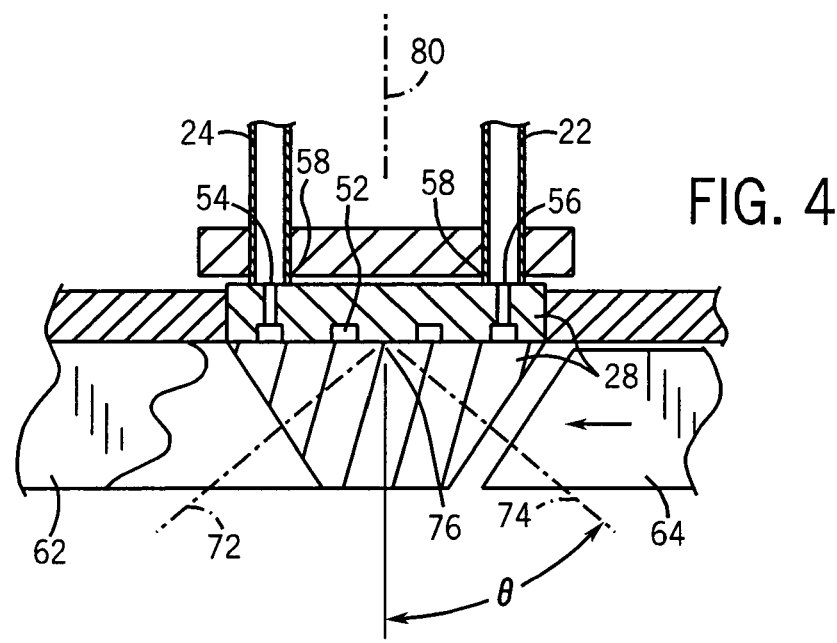
FIG. 4 is a fragmentary, front elevational cross section of the sample cell of FIG. 3 installed in the housing of FIG. 2, showing retraction of a clamp holding the sample cell and showing an O-ring seal connecting the sample cell to an interface plate.

Referring also to FIGS. 3 and 4, the integrated test cell 28 is contained within the housing 18 beneath a top wall of the housing 18 to be generally shielded from the environment and ambient light. An upper face of the integrated test cell 28 is held against a lower face of the interface plate 32 so that the sample inlet port 22 attached to the interface plate 32 aligns with a cell inlet port 54 of the integrated test cell 28 and the sample outlet port 24 attached to the interface plate 32 aligns with a cell outlet port 54 of the integrated test cell 28. O-rings 58, fitting in shallow toroidal grooves in the interface plate 32, provide a seal when the integrated test cell 28 is pushed upward against the interface plate 32 as will be described below.

Referring now to FIG. 3, the integrated test cell 28 includes an optical prism 40 being generally a triangular prism having a base face 42a and two side faces 42b and 42c whose planes together define an isosceles triangular prism. In the preferred embodiment, the apex of the prism 40 representing the junction between faces 42b and 42c may be flattened or truncated to save material and space. The prism 40 is preferably constructed of a transparent plastic of high refractive index such as polystyrene.

A gold film 44 is deposited on the base face 42a and forms the metallic film needed for SPR measurement. A series of stripes or patches of probe molecules 48, for example single-stranded DNA containing a sequence complementary to a sequence of interest, are then deposited on the exposed surface of the gold film 44 (the sensing surface) according to methods well known in the art.

A flow cell block 50 may have a serpentine channel 52 cut in a surface facing face 42a to attach to face 42a to define a serpentine fluid path adjacent to the gold film 44 and crossing the strips of probe molecules 48. Cell inlet port 56 and cell outlet port 54 are holes in the flow cell block 50 communicating with the serpentine channel 52 at the ends of the serpentine channel 52 and pass through the flow cell block 50 to its upper face removed from the prism 40. For field use, the flow cell block 50 is preferably permanently attached to the prism 40 by adhesive or mechanical means so as to limit the possibility of contamination of the contained fluid path and probe molecules. Prior to use, an adhesive label (not shown) may be placed on the upper surface of block 50 to prevent contaminants from entering into the cell inlet port 56 and cell outlet port 54.

Preferably, the integrated test cell 28 is disposable and freely replaceable so as to allow multiple tests or tests using different probe molecules 48. For this reason, in the preferred embodiment, the integrated test cell 28 is releasably held by a clamp 60 attached to a lower surface of an upper wall of the housing 18. The clamp 60 includes a first set of fixed, sloped, registration jaws 62 attached to the housing and abutting face 42c of the integrated test cell 28 to orient the face 42a to be parallel the lower surface of the interface plate 32. A second set of jaws 64, having a similar slope, are moveable in a horizontal direction 65 by a captive knurled nut 66 acting on a screw 68 attached to the movable jaws 64. Rotation of the knurled nut 66 advances or retracts the movable jaws 64 toward and away from the integrated test cell 28. The sloping faces of the registration jaws 62 and movable jaws 64 cause the horizontal compression of the integrated test cell 28 between the registration jaws 62 and movable jaws 64 to yield an upward force compressing the interface between the integrated test cell 28 and interface plate 32.

The upper wall of the housing 18 to which the registration jaws 62, movable jaws 64, and interface plate 32 are attached, may hinge upward as indicated by arrow 116 about hinge point 118 to allow easy access to the integrated test cell 28 for changing the integrated test cell 28.

Referring generally to FIG. 3, registration jaws 62 and movable jaws 64 (not shown in FIG. 3) are bifurcated, providing a central, unobstructed light path 70 to the faces 42c and 42b along tipped optical paths 72 and 74 intersecting at a point 76 on the surface of the gold film 44 shown in FIG. 4.

Referring again to FIG. 2, first swing arms 82 attaches at pivot 84 to the front and back of the integrated test cell 28 defining an axis intersecting point 76 (shown in FIG. 4). The swing arms 82 move so that a housing 86 attached at a free end of the swing arms 82 removed from the pivot 84 swings in a radius about point 76. Housing 86 contains a light emitting diode (LED) 88, preferably emitting light in the infrared region. The light from the LED 88 is directed through a polarizer 90 along the optical path 72 toward the point 76. Light from the LED 88 passes through face 42c of the prism 40 to strike and illuminate the area of the gold film 44. The angle of the optical path will be approximately, but not necessarily, exactly perpendicular to the face 42c for maximum light transmission into the prism 40 with minimal reflection at face 42c.

Light reflected from the surface of the gold film attached to the prism 40 of the integrated test cell 28 exits along optical path 74 approximately perpendicular to the face 42b for maximum light transmission into the air with minimal internal reflection at face 42b. The light is passed through a monochromatic filter 91 having transmission characteristics centered at the peak emission of the diode 88. This light is received by a charge couple device (CCD) camera 92 or other similar electronic camera contained within a housing 94 and directed back along the optical path 74. The camera 92 and housing 94 supporting it, is held by swing arms 96 also attached to pivot 84. As so attached, the housing 94 and camera 92 swing in a radius about point 76 (shown in FIG. 4) so that the camera 92 may receive an image of the gold film 44 around point 76.

The camera 92 may be moved radially along optical path 74 by means of a slide mount 98 supported for linear motion within the housing 94 and moved by a machine screw 100 whose head is retained by housing 94 and whose threads move the slide mount 98 against the bias of a helical spring 102 captured between the housing 94 and the slide mount 98. The camera 92 may include a replaceable lens assembly 104 allowing the field of view of the gold film 44 to be changed. The slide mount 98 allows accurate focusing of the camera on the surface of the gold film 44.

The pivots 84 for the swing arms 82 and 96 are attached to side walls of the housing 18 to allow the upper wall of the housing 18 to swing upward.

Generally, as will be described now, during movement of the swing arms 82 and 96, optical paths 72 and 74 are maintained in equal angular relationship with respect to a normal 80 to the surface 42a to maximize the reflected light received by the camera 92 from the LED 88. Within this equality constraint, the angle between each optical path 72 and 74 and the normal 80, hereafter referred to as θ, may also be adjusted to maximize the sensitivity of the camera 92 to changes in reflected light.

Adjustment of the angle θ of optical path 72 and 74 while maintaining them in equal relationship to the normal 80 is provided by means of a gear system including two counter-rotating, inter-engaging gears 106 and 108. Gear 108 communicates via shaft through a sidewall of the housing 18 with knob 20 to be directly turned by a user while gear 106 turns as driven by gear 108.

Spur gears 109 and 110 are attached coaxially to gears 106 and 108, respectively, to turn therewith, and engage arcuate racks 112 and 114 having radii centered at pivot 84 and attached to swing arms 82 and 96, respectively. Rotation of gear 108 causes equal and opposite rotation of gear 106 with corresponding rotations of gears 110 and 109 operating on arcuate racks 112 and 114 to ensure equiangular motion of swing arms 96 and 82.

Figure 5:
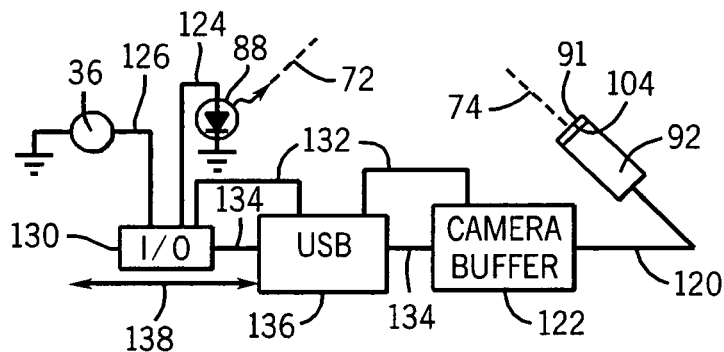
FIG. 5 is a schematic block diagram of the circuitry of the device of FIGS. 1 and 2 showing connection of both power and data.

Referring now to FIGS. 2 and 5, camera 92 may communicate through wiring 120 with a camera buffer board 122 also contained within the housing 18. The wiring 120 is flexible and held loosely in the housing 18 to allow movement of the camera 92 radially and angulation. Likewise, the LED 88 and pump 36 communicate via wiring 124 and 126 with an I/O interface board 130 providing switched power for each according to methods well known in the art. The I/O interface board 130 and camera buffer board 122 in turn through power wiring 132 and data wiring 134 with a USB interface board 136 connected with a standard USB interface cable 138 such as provides a path of data communication of image data from the camera 92 and a source of power for the camera 92, LED 88 and pump 36, from the power supply of the attached computer, for example, the battery of the laptop computer 16, and signals from the computer controlling the pump 36 and LED 88. Alternatively, the pump 36 and LED 88 may be switched by electrical switches located at the analyzer unit 12.

Figure 6:
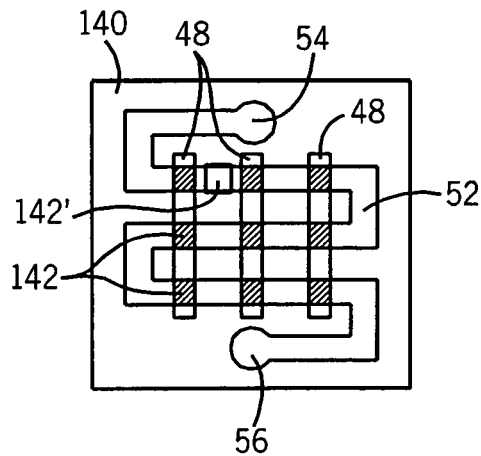
FIG. 6 is a simplified display of an image obtained by the camera of FIG. 2 displayed on the display of the laptop of FIG. 1 showing sample regions defined by an intersection between strips of probe molecules and a serpentine sample path.

Referring now to FIGS. 2 and 6, when the LED 88 is illuminated, the camera 92 will provide an image 140 of the surface of the gold film 44 adjacent to the prism 40. This image 140 may be communicated to the standard laptop computer to be displayed during an adjustment after introduction of the sample solution. As shown in FIG. 6, the image 140 will reveal one or more regularly spaced regions 142 being intersections of the serpentine channel 52 and the strips of probe molecules 48. Generally, the probe molecules 48 will include both those that will attach to target molecules in the sample material as well as those that do not attach to target molecules so as to provide further discrimination with respect to the target molecules. In addition, other control regions 142' may be located between the strips of probe molecules 48 within or outside of the serpentine channel 52 to provide control and baseline region.

Figure 8:
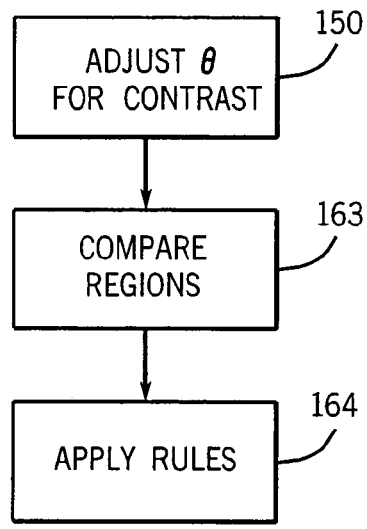
FIG. 8 is the flowchart showing the principal steps of analyzing sample material using the present invention.

As indicated by the first process block of FIG. 8, as indicated by process block 150, after the sample material has been washed through the integrated test cell 28, the image 140 may be observed and the contrast between the sample regions 142 (and 142') may be adjusted by changing the angulation of the camera 92 and LED 88 using knob 20. While the present invention provides a mechanical adjustment, it will be understood that this adjustment can also be done under computer control using an electric motor in place of knob 20.

Figure 7:
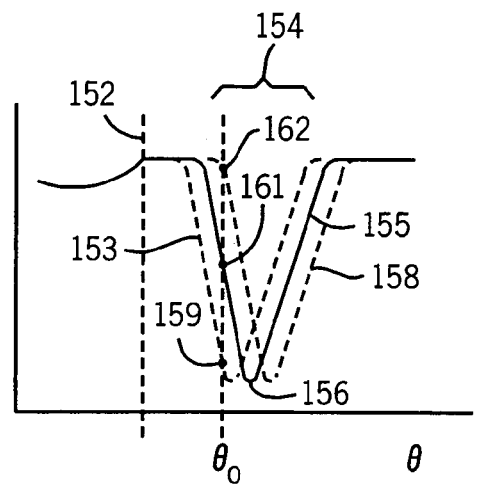
FIG. 7 is a plot of percent reflection versus angle of reflection showing adjustment of the angle for maximum contrast between the sample regions of FIG. 6.

Referring to FIG. 7, the reflection off of the gold film 44 as a function of θ will follow a curve 155 that will remain relatively constant after a critical angle 152 is reached and until a region of plasmon resonance 154. At this point, interaction between the electron resonance and the material on the opposite side of the gold film 44 causes absorption of some proportion of the reflected light. For a given amount of material on the sensing side of the gold film 44, for example, amount represented by the attached probe molecules 48, this reflectance will have a minimum 156 at a particular angle θ.

The addition of material to the sensing side of the gold film 44 caused, for example, by binding between the probe molecules 48 with the target molecules, will cause the angular dependence of light reflection to shift left as indicated by curve 153 (dashed line) with a minimum 160. The removal of material to the sensing side of the gold film 44 caused, for example, by regions 142' having no probe molecules 48, will cause the reflection of light to shift right as indicated by curve 158 (dashed line).

At process block 150, the angulation of the optical axis may be adjusted to a $θ_0$ point 161, for example, at a steep part of the curve 155 at which the reflection is between 100% and the minimum 156 in an area with probe molecules 48 prior to binding of the probe molecules 48 and target molecules. In this case, an increase in binding causing a shifting to curve 158, will produce a significant increase in reflectance as indicated by point 162 from point 161. Conversely, regions 142 having neither probe molecules nor target molecules will reveal themselves as regions having no change in reflection.

Clearly, a variety of different starting points 161 may be provided on both sides of the slopes leading to the resonance point minima 156 and 160 to obtain contrast that may be measured. Generally, it will be important to approach the resonant point from a consistent direction so as to maintain the proper sense between regions 142 having a build up of molecular material and those relatively free of molecular material.

In an alternative embodiment, the range angular values θ may be swept, either manually or with a motor communicating with gear 110, and using an angular resolver to provide data to the computer 16, values $θ_i$ for each minima for each region 142 can be determined and these values $θ_i$ used for differentiation.

Referring now to process block 163 of FIG. 8, reflectance at each of the regions 142 is then compared to control regions, or a previously acquired control image to normalize the measurements. Thresholds are applied to identify each region as binding or non-binding and at process block 164 a set of rules is applied to the region characterizations, being in a simplest case, a Boolean statement with region characterizations as binding vs. non-binding used as arguments. For example, if accumulation of material is obtained on a region 142, not on a second or third region 142, this may indicate a particular material in the target sample.

Figure 9:
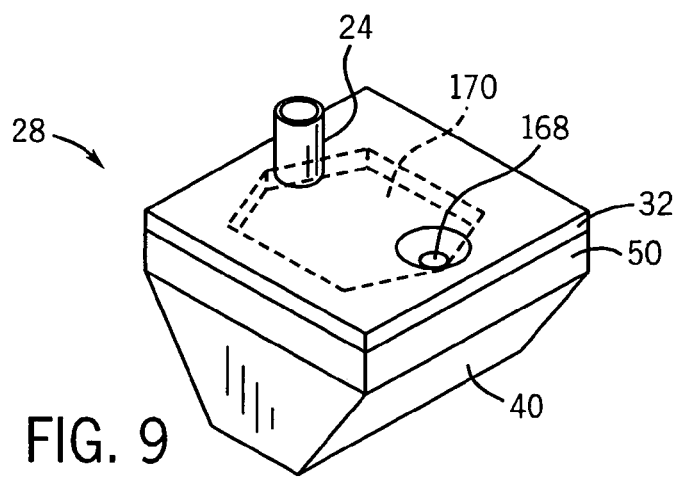
FIG. 9 is an alternative embodiment of the sample cell of FIGS. 4 and 3, showing an open area chamber design and the use of a well and integrated interface plate.

Referring now to FIG. 9 in an alternative embodiment, the interface plate 32 of FIG. 2 may be incorporated directly into the flow cell block 50 of FIG. 3 to eliminate an additional element subject to contamination. Sample inlet port 22 and outlet port 24 may be integrally incorporated into the interface plate 32 or as shown, the inlet port 22 may be replaced with a shallow receiving well 168 into which extremely small samples may be placed by pipette or the like. Generally the small samples will preferably be used with the serpentine path of the serpentine channel 52 of FIG. 3, however, FIG. 9 also shows an alternative broad area straight channel 170 such as may be useful in certain circumstances.

The features of the present invention combine to provide a low cost and compact unit that may be used with standard computers to provide for SPR measurements in the field. Such a device may be used in a handheld fashion or may be attached to remote devices such as robots or the like for field sampling. Different measurements for different targets may be made by simply replacing the integrated test cell 28. Alternatively, repeated measurements for the same target over time may be made by use of identical, but new integrated test cells 28.

It is specifically intended that the present invention not be limited to the embodiments and illustrations contained herein, but include modified forms of those embodiments including portions of the embodiments and combinations of elements of different embodiments as come within the scope of the following claims.

We claim:

1. A portable surface plasmon resonance imaging system comprising:

a housing sized to be supported in one hand;

a sampling cell held by the housing and having a metallic film having probe molecules attached to a first side exposed to material flow through the sampling cell and having a transparent support attached to a second side opposite the first side held within the housing to be shielded from ambient light;

a light emitting diode light source supported within the housing on a first swing arm pivoting in a radius about a point on the surface of the metallic film of the sampling cell to illuminating a region about the point through the transparent support;

an electronic camera supported within the housing on a second swing arm pivoting in a radius about the point on the surface of the metallic film of the sampling cell and receiving reflected light from the second side of the metallic film;

a registration means releasably accepting and orienting the sampling cell in a predetermined orientation with respect to the first and second swing arms; and and a mechanism between the first and second swing arms to move them simultaneously in symmetrical opposition about a normal to a surface of the metallic film with manipulation of a single operator.

2. The portable surface plasmon resonance imaging system of claim 1 wherein the operator is a rotary operator and wherein the mechanism is a pair of engaging and counter-rotating gears, each gear communicating, respectively, with an arcuate rack attached to one of the swing arms.

3. The portable surface plasmon resonance imaging system of claim 1 wherein the electronic camera includes a lens adjustment allowing change of field of view of the electronic camera.

4. The portable surface plasmon resonance imaging system of claim 1 wherein the light emitting diode is infrared diode.

5. The portable surface plasmon resonance imaging system of claim 1 further including a cable connecting the electronic camera and the light emitting diode to a general purpose computer, the cable including power leads communicating power from a power source contained in the computer to the electronic camera and light emitting diode for powering the same.

6. The portable surface plasmon resonance imaging system of claim 5 wherein the cable further includes data leads communicating an image signal from the electronic camera to the computer, and further including a program executable on the computer to read an image from the electronic camera and process the image to detect binding of a test material to the probe molecules on the metallic film.

7. The portable surface plasmon resonance imaging system of claim 6 wherein the probe molecules are deposited in predetermined locations on the metallic film and wherein the program in the portable computer compares images received from the predetermined locations and from second predetermined locations not having the probe molecules.

8. The portable surface plasmon resonance imaging system of claim 1 further including a pump communicating with the sampling cell to pass a sampled material past the metallic film.

9. The portable surface plasmon resonance imaging system of claim 1 wherein the sampling cell is a prism and the housing includes a clamp providing a fixed registration surface interfitting with at least two of the faces of the prism to fix the prism at a predefined location.

10. The portable surface plasmon resonance imaging system of claim 9 wherein the prism is formed of a transparent polymer.

11. The portable surface plasmon resonance imaging system of claim 9 wherein the prism further includes an integral flow cell portion defining a cavity next to the side of the metallic film having the attached probe molecules for the flow of sample material from a flow cell inlet to a flow cell outlet.

12. A portable surface plasmon resonance imaging system suitable for field use comprising: a housing sized to be supported in one hand;
a sampling cell held by the housing and having a metallic film having probe molecules attached to a first side exposed to material flow through the sampling cell and having a transparent support attached to a second side opposite the first side held within the housing to be shielded from ambient light;
a light source supported within the housing on a first swing arm pivoting in a radius about a point on the surface of the metallic film of the sampling cell to illuminating a region about the point through the transparent support the light source including a light-emitting diode and a polarizer;
an electronic camera and monochromatic filter supported within the housing on a second swing arm pivoting in a radius about the point on the surface of the metallic film of the sampling cell and receiving reflected light from the second side of the metallic film;
and a mechanism between the first and second swing arms to move them simultaneously in symmetrical opposition about a normal to a surface of the metallic film;
a cable extending out of the housing and connecting the electronic camera and the light source to a general purpose computer, the cable including a power lead communicating power from a battery contained in the general purpose computer to the electronic camera and light source for powering the same and data leads communicating image signals of the electronic camera.

13. The portable surface plasmon resonance imaging system of claim 12 wherein the cable is a universal serial bus cable and wherein the electronic camera connects to the cable to send image data over a universal serial bus interface.

14. The portable surface plasmon resonance imaging system of claim 12 wherein the light emitting diode is infrared diode.

15. The portable surface plasmon resonance imaging system of claim 12 wherein the cable further includes data leads communicating an image signal from the electronic camera to the computer, and further including a program executable on the computer to read an image from the electronic camera and process the image to detect binding of a test material to the probe molecules on the metallic film.

16. The portable surface plasmon resonance imaging system of claim 15 wherein the probe molecules are deposited in predetermined locations on the metallic film and wherein the program in the portable computer compares images received from the predetermined locations and from second predetermined locations not having the probe molecules.

17. The portable surface plasmon resonance imaging system of claim 12 further including a pump communicating with the sampling cell to pass a sampled material past the metallic film, wherein the power leads of the cable also communicate power from the power source contained in the computer to the pump for powering the same.

18. The portable surface plasmon resonance imaging system of claim 12 wherein the sampling cell is a prism and the housing includes a clamp providing a fixed registration surface interfitting with at least two of the faces of the prism to fix the prism at a predefined location.

19. The portable surface plasmon resonance imaging system of claim 18 wherein the prism further includes an integral flow cell portion defining a cavity next to the side of the metallic film having the attached probe molecules for the flow of sample material from a flow cell inlet to a flow cell outlet.

20. The portable surface plasmon resonance imaging system of claim 12 wherein the prism is formed of a transparent polymer.

* * * * *